United States Patent
Perouse et al.

(10) Patent No.: US 7,927,317 B2
(45) Date of Patent: Apr. 19, 2011

(54) INJECTION DEVICE WITH EXTRACTION MECHANISM

(75) Inventors: Eric Perouse, Paris (FR); Thomas Walter, Rueil-Malmaison (FR)

(73) Assignee: Laboratories Perouse, Ivry le Temple (FR)

( * ) Notice: Subject to any disclaimer, the term of this patent is extended or adjusted under 35 U.S.C. 154(b) by 0 days.

(21) Appl. No.: 11/579,441

(22) PCT Filed: May 2, 2005

(86) PCT No.: PCT/FR2005/001096
§ 371 (c)(1),
(2), (4) Date: May 14, 2008

(87) PCT Pub. No.: WO2005/120624
PCT Pub. Date: Dec. 22, 2005

(65) Prior Publication Data
US 2008/0269695 A1  Oct. 30, 2008

(30) Foreign Application Priority Data
May 7, 2004  (FR) ..................... 04 04975

(51) Int. Cl.
*A61M 5/00* (2006.01)
*A61M 5/32* (2006.01)
*A61M 31/00* (2006.01)
*A61M 37/00* (2006.01)

(52) U.S. Cl. ................. 604/263; 604/192; 604/93.01

(58) Field of Classification Search ............ 604/164.04, 604/177, 263, 272, 93.01, 192
See application file for complete search history.

(56) References Cited

U.S. PATENT DOCUMENTS

| 5,584,813 | A | | 12/1996 | Livingston et al. |
| 5,879,330 | A | * | 3/1999 | Bell ..................... 604/93.01 |
| 5,997,504 | A | | 12/1999 | Bell |
| 6,090,068 | A | * | 7/2000 | Chanut ................. 604/93.01 |
| 6,261,259 | B1 | * | 7/2001 | Bell ..................... 604/93.01 |
| 6,824,530 | B2 | * | 11/2004 | Wagner et al. ........... 604/162 |
| 6,997,902 | B2 | * | 2/2006 | Thorne et al. ........... 604/110 |
| 7,229,434 | B2 | * | 6/2007 | Wang .................... 604/263 |
| 7,717,888 | B2 | * | 5/2010 | Vaillancourt et al. ...... 604/263 |
| 2002/0072716 | A1 | * | 6/2002 | Barrus et al. ............ 604/192 |
| 2003/0083624 | A1 | * | 5/2003 | Smith et al. ............. 604/177 |
| 2004/0087912 | A1 | * | 5/2004 | Swenson ................. 604/263 |
| 2004/0158207 | A1 | | 8/2004 | Hunn et al. |
| 2004/0215154 | A1 | * | 10/2004 | Hwang et al. ............ 604/263 |
| 2004/0260250 | A1 | * | 12/2004 | Harris et al. ............ 604/263 |
| 2004/0267210 | A1 | * | 12/2004 | Popovsky ............... 604/263 |

FOREIGN PATENT DOCUMENTS

FR  2 781 378  1/2000
WO  02/081012  10/2002

* cited by examiner

*Primary Examiner* — Nicholas D Lucchesi
*Assistant Examiner* — William Carpenter
(74) *Attorney, Agent, or Firm* — Wenderoth, Lind & Ponack, L.L.P.

(57) ABSTRACT

An injection device comprises: a needle support; an injection needle which is fixedly joined to the needle support and which has a free end which is arranged with spacing from the needle support; and a mechanism for extracting the injection needle, comprising a base and a pushing member which can be moved relative to the base between a position in which the needle is used and a position in which the needle is extracted. The base is permanently connected to the needle support and can be moved relative to the needle support between an inactive position of the extraction mechanism and an active position of the extraction mechanism.

19 Claims, 4 Drawing Sheets

INJECTION DEVICE WITH EXTRACTION MECHANISM

The present application is a national stage entry of PCT/FR2005/001096, filed May 2, 2005, and claims priority benefits under 35 U.SC. 119(a)-(d) to FR0404975, filed May 7, 2004.

BACKGROUND OF THE INVENTION

1. Field of the Invention

The present invention relates to an injection device which comprises:
a needle support;
an injection needle which is fixedly joined to the needle support and which has a free end which is arranged with spacing from the needle support; and
a mechanism for extracting the injection needle, the mechanism comprising a base and a pushing member which can be moved relative to the base between a position in which the needle is used and a position in which the needle is extracted.

2. Background Art

In some pathological fields, it is necessary to inject daily a liquid dose of medication directly into an organ of a patient. To this end, it is known to permanently implant, in the chest of the patient, a chamber which is arranged beneath the skin. This chamber is extended with a tube which leads from the support to the organ where the dose of medication has to be delivered. The chamber which can be implanted comprises a container which has a cover perforatable along the surface thereof which is in contact with the skin.

In order to inject the dose of medication, the needle of the device is engaged through the skin of the patient into the implantable chamber and the dose of medication is injected into this chamber through the needle.

In order to carry out injections of this type, an injection device is commonly used which comprises a support which is fixedly joined to the needle. The support is extended by a tube, one end of which is connected to the injection needle and the other end of which is provided with a connector which allows the connection of a syringe or a container of a dose of medication to be injected.

In order to extract the needle from the implantable chamber, the practitioner grips the support of the device and pulls the needle out of the support of the patient.

However, since the membrane of the implantable chamber is relatively strong, a significant pulling force must be applied to the needle in order to allow it to be extracted. In order to prevent the patient from being in discomfort owing to the forces applied to the skin by the implantable chamber when the needle is removed, it is known to use an extraction mechanism as described in document FR 2 781 378.

After being fixedly joined to the needle support, the extraction mechanism comprises a base and a pushing member which can be moved along the length of the needle. The extraction mechanism is positioned and fixedly joined to the needle support only immediately before proceeding to remove the needle from the implantable chamber. The extraction mechanism cannot be left permanently since the space occupied by the pushing member which generally extends parallel with the axis of the needle forms a relatively high projection above the support. The pushing member thus protrudes relative to the skin of the patient, preventing a dressing from being readily placed over the injection device. In the same manner, the protruding pushing member impedes the movements of the patient.

BRIEF SUMMARY OF THE INVENTION

The positioning of the extraction mechanism on the needle support is a complex operation since the needle is engaged in the implantable chamber and it has occasionally been found that the extraction mechanism has been mispositioned when it is used.

The object of the invention is to provide an injection device which prevents accidental occurrences of pricking and which does not have the disadvantages of difficulties in terms of positioning the extraction mechanism.

To this end, the invention relates to an injection device of the above-mentioned type, characterised in that the base is permanently connected to the needle support and can be moved relative to the needle support between an inactive position of the extraction mechanism and an active position of the extraction mechanism.

According to specific embodiments, the device comprises one or more of the following features:
the base delimits a passage for movement of the pushing member, in which the pushing member is received so as to slide between the position in which the needle is used and the position in which the needle is extracted;
the injection needle is mounted on a head at the end of the needle support, the head being visible in the inactive position of the extraction mechanism;
the base is articulated with the needle support;
the pushing member is generally elongate, and the pushing member extends in a plane which is generally perpendicular relative to the main portion of the needle, when the base is in the inactive position of the mechanism;
the pushing member is generally hollowed out and the needle support comprises a core which is at least partially received in the pushing member when the base is in the inactive position of the mechanism;
the needle support and the base comprise complementary resilient engagement means which are capable of temporarily retaining the base relative to the needle support in the inactive position of the extraction mechanism and/or in the active position of the extraction mechanism;
the base comprises radial extensions which form finger supports;
the pushing member can be moved in a sliding manner relative to the base;
the base and the pushing member comprise complementary resilient engagement means which are capable of temporarily retaining the pushing member relative to the base in the position thereof in which the needle is extracted and/or in the position thereof in which the needle is used.

BRIEF DESCRIPTION OF THE DRAWINGS

The invention will be better understood from a reading of the following description, given purely by way of example and with reference to the appended drawings, in which.

FIGS. 1, 2 and 3 illustrate an injection device 10 according to the invention, connected to an implantable chamber 12.

DETAILED DESCRIPTION OF THE INVENTION

Figure 1:
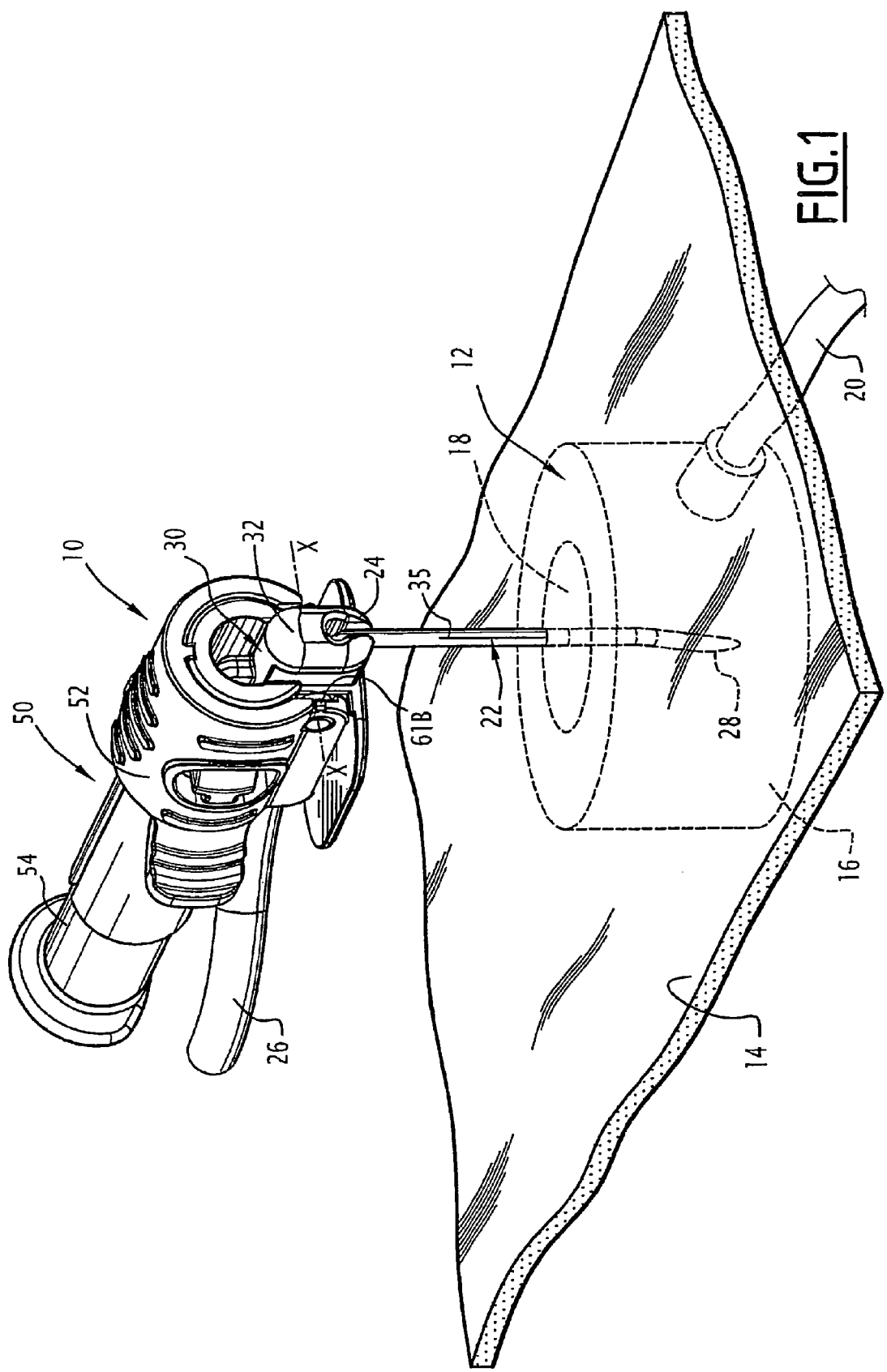
FIGS. 1 and 2 are perspective and front views, respectively, of an injection device according to the invention, connected to an implantable chamber when a liquid is injected.
Figure 2:
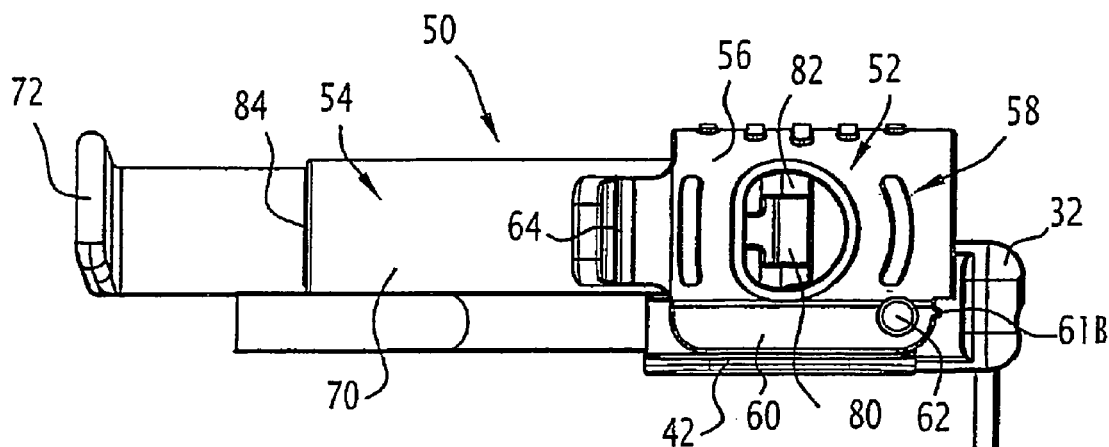
Figure 3:
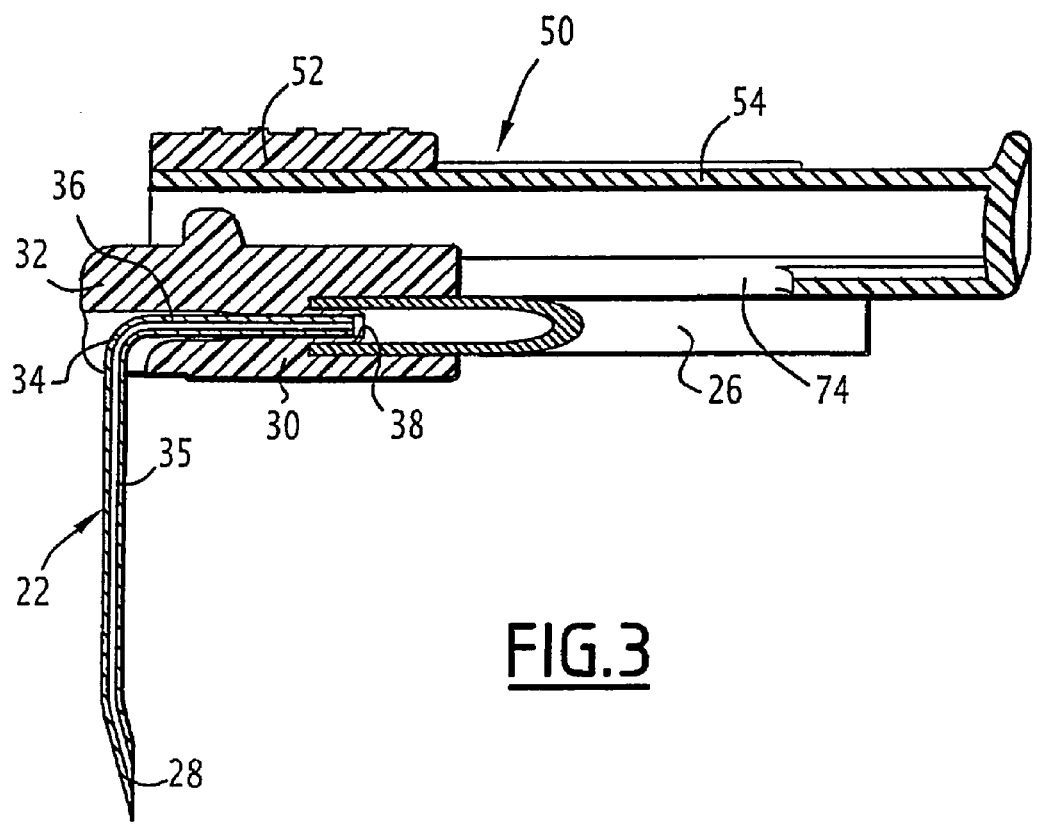
FIGS. 3 and 4 are a longitudinal section and a top view of the injection device.
Figure 4:
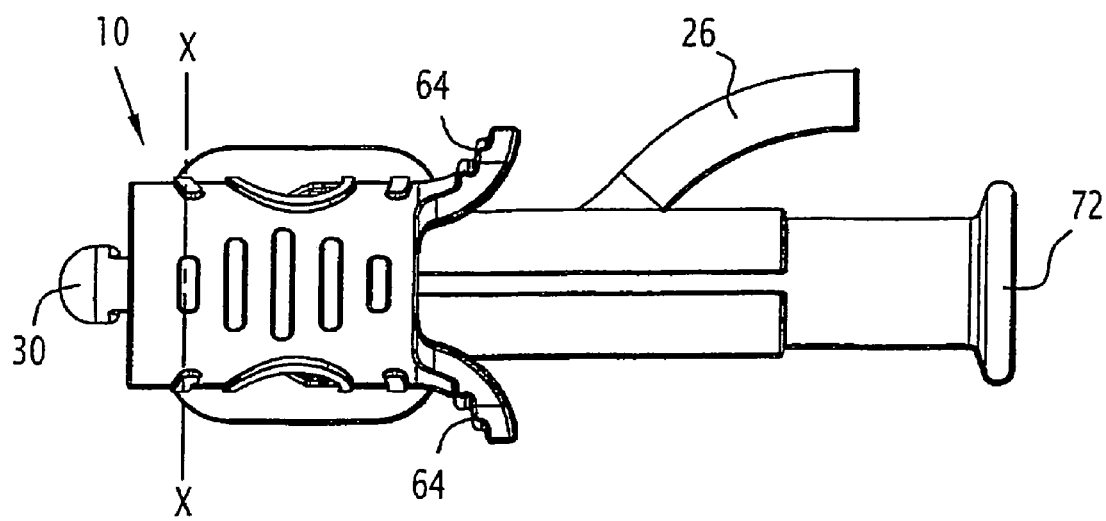

The chamber 12 is arranged beneath the skin designated 14 of a patient. This chamber has a container 16 which is generally cylindrical and which is delimited, on the face thereof in contact with the inner surface of the skin, by a perforatable membrane 18. The container 16 is connected to a tube 20 for conveying a solution of medication to an affected organ.

The injection device comprises a needle 22 which is fixedly joined to a needle support 24 which is extended with a catheter 26 which is connected to the needle 22.

The needle 22 has a curved free end 28 so that it opens laterally relative to the general axis of the needle.

The support 24 comprises a central core 30 which is elongate and generally cylindrical and through which an axial conduit extends from one side to the other for conveying liquid to the needle 22. The needle 22 is fixedly joined to an end of the core 30 which forms a head 32.

The needle 22 forms an elbow-like joint 34 which is extended at the side of the tip 28 by a main portion 35 and, at the side remote from the tip 28, by a perpendicular connection section 36 which is engaged in the axial conduit which extends through the core 30, from the head 32. At the other end thereof, the conduit is extended by a stud 38 which brings about the connection of the catheter 26.

At the side of the support directed towards the needle 22, the support 24 comprises a support plate 42 which extends along the length of the support with the exception of the end region which forms a head which protrudes relative to this support plate 42.

Figure 5:
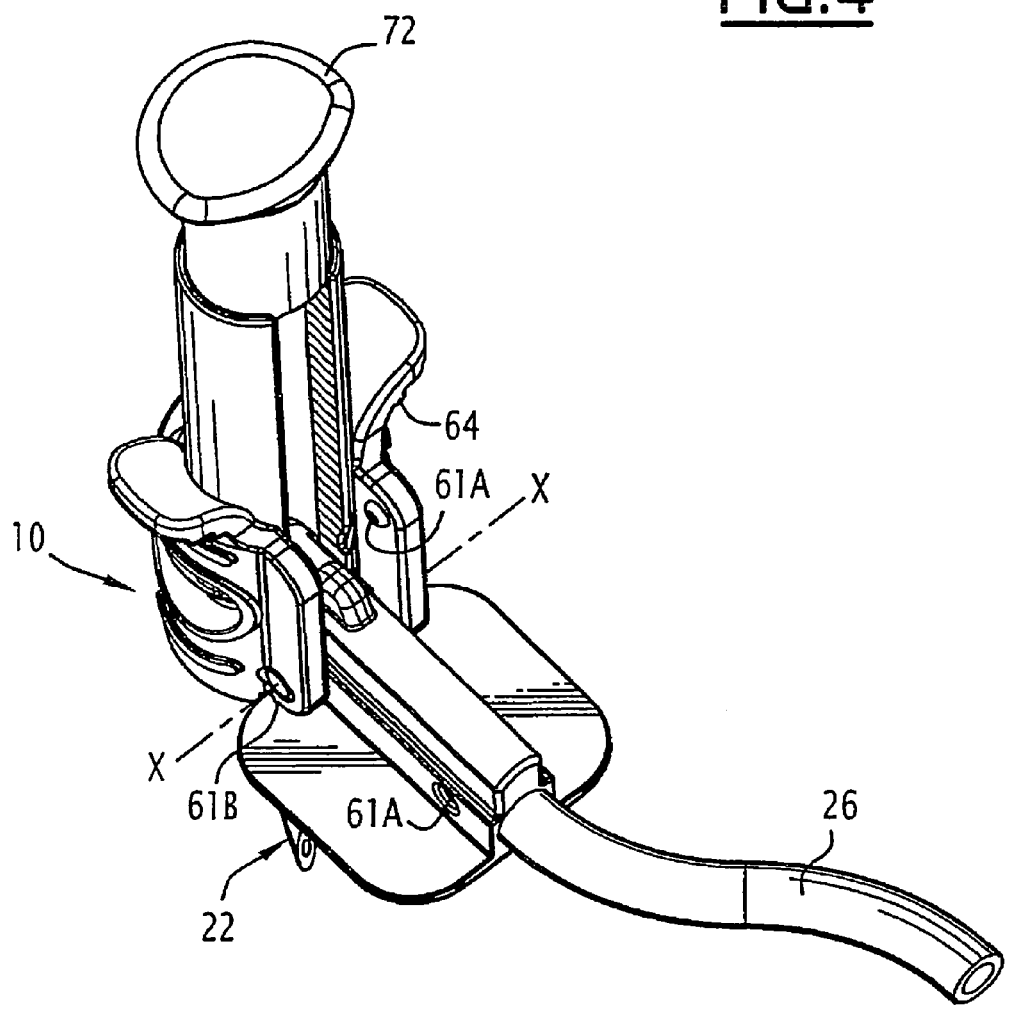
FIGS. 5 and 6 are a perspective view and a sectioned view, respectively, of the injection device, immediately before the needle is extracted.
Figure 6:
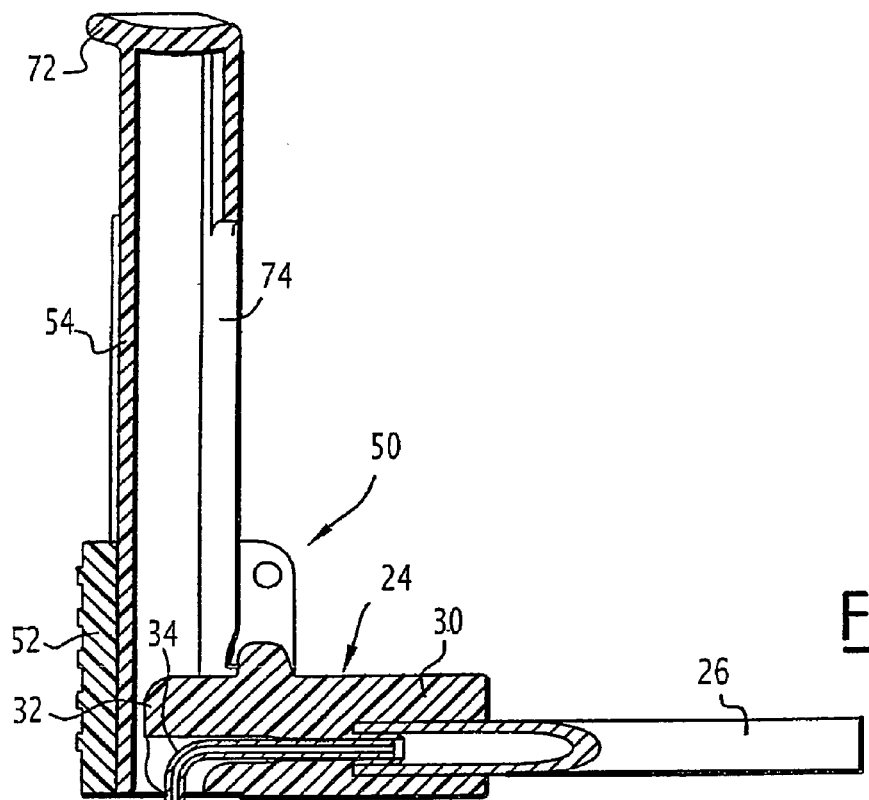
Figure 7:
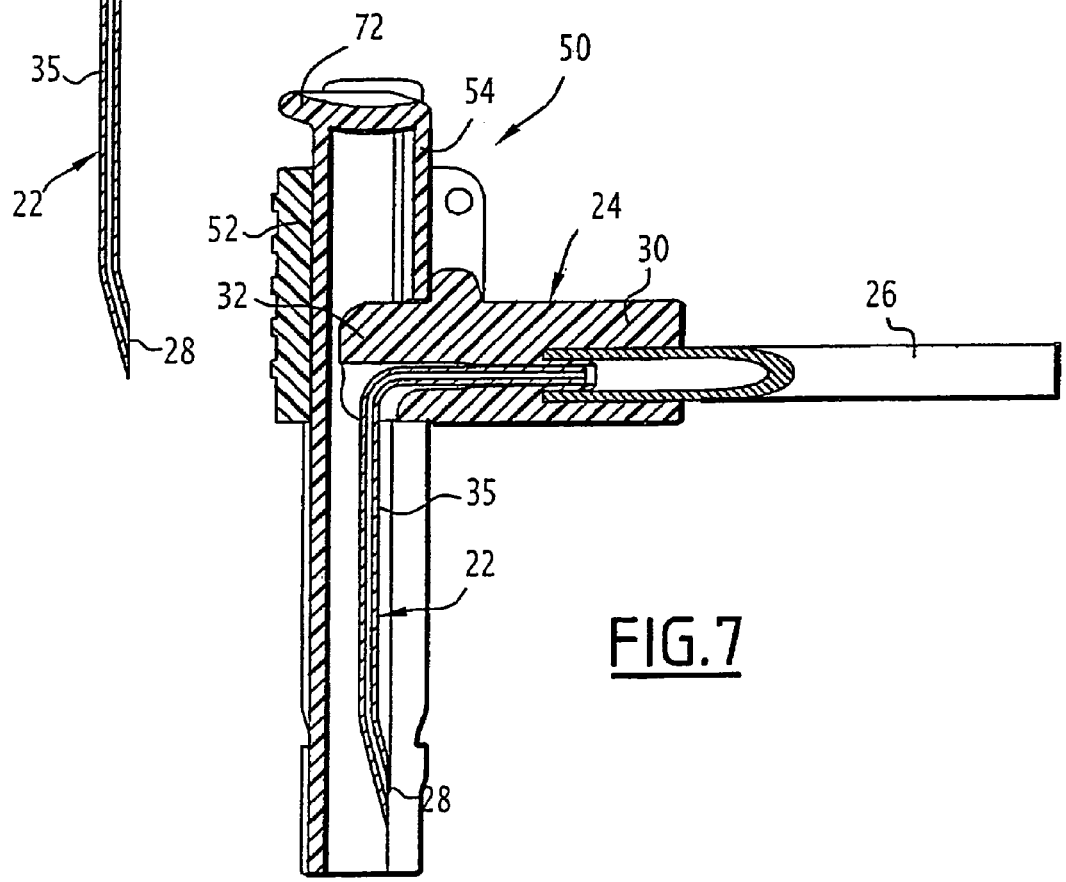
FIG. 7 is a sectioned view of the injection device after use and in a condition to be discarded.

According to the invention, the injection device 10 comprises a mechanism 50 for extracting the needle 22 which is permanently connected to the needle support 24, being able to be moved relative thereto between an inactive position of the extraction mechanism as illustrated in FIGS. 1 to 4 and an active position of the extraction mechanism as illustrated in FIGS. 5 to 7.

The extraction mechanism 50 comprises a base 52 and a pushing member 54 which is mounted so as to slide relative to the base 52. The base 52 can be moved relative to the support 24 and is in particular articulated relative thereto about an axis X-X which extends perpendicularly relative to the plane of the curved needle 22.

The base 52 is formed by a sleeve 56 which delimits a passage 58 for movement of the pushing member 54. The sleeve 56 is open laterally along a generating line over a width which corresponds to the width of the central core 30 of the support.

At one side and the other of this opening, the sleeve is extended by two walls 60 which are capable of engaging around the central core 30. In order to articulate the base to the central core, the walls 60 are perforated by two circular holes in which studs 62 are received which are integral with the central core and which extend along the articulation axis X-X. The articulation axis is located beside the region of the head 32 so that, in a tilted position, the head 32 extends inside the passage 58.

Protruding profile-members in the form of complementary hollow members 61A, 61B for resilient engagement are provided on the walls 60 and the support 24 in order to temporarily immobilise the extraction mechanism, both in the active position and in the inactive position thereof.

At the end thereof remote from the head 32, the sleeve has, at the outer side, two radial protuberances which form a finger support 64.

The pushing member 54 is formed by a rod 70 which is generally hollowed out and open at one end which is referred to as the front end and which is directed towards the needle 22. It is closed at the rear end thereof by a finger support 72. The rod 70 is open, from the front end thereof, by an aperture 74 which extends along the length of the pushing member over the main part of the length thereof. The width of the aperture is sufficient to receive the central core 30.

The pushing member 54 is received so as to slide inside the passage 58 delimited by the base 52 between a position in which the needle is used as illustrated in FIGS. 1 to 4, and a position in which the needle is extracted as illustrated in FIGS. 5 to 7.

In the position in which the needle is used, the open end of the pushing member is located in the region of the base 24, whilst, in the extraction position, the end closed by the pushing member 54 is in the region of the base 52, the open end extending beyond the tip 28 of the needle.

The base 52 and the pushing member 54 comprise complementary resilient engagement elements which are capable of temporarily retaining the pushing member in the two extreme positions thereof for use and extraction. For example, these means for resilient engagement comprise tongues 80 which can be resiliently deformed and which are integral with the base 52. These tongues protrude towards the inner side of the passage 58. The pushing member 54 comprises shoulders 82, 84 which are capable of allowing engagement of the tongues 80 behind these shoulders in order to immobilise the pushing member in the positions thereof for use and extraction.

Initially, the extraction mechanism 50 is in the inactive position thereof, with the pushing member 54 extending generally perpendicularly relative to the main portion 35 of the needle 22, being positioned along the length of the central core 30. In this position, the walls 60 of the base 52 press on the plate 42.

The pushing member is then in its position in which the needle is used so that the head 30 is visible.

In this position, the needle 22 of the injection device can be introduced into an implantable chamber 12 and depressed until the plate 42 presses on the skin of the patient. The presence of the extraction mechanism folded along the length of the central core of the needle support does not impede handling. Furthermore, since the pushing member 54 is folded down along the central core, it does not protrude along the entire length thereof relative to the skin of the patient so that the injection device, after being positioned, can be readily held by means of an adhesive strip.

In order to withdraw the injection device, the extraction mechanism is straightened and moved into the active position thereof. To this end, the base 52 and the pushing member 54 are tilted about the axis X-X in order to be moved into the position illustrated in FIGS. 5 and 6. The pushing member 54 is in the axis of the main portion 35 of the needle, and the two extensions 64 extend generally perpendicularly relative to the axis of the main portion of the needle. The head 32 of the support is received in the hollowed out pushing member 54. In this position, the operator holds the extraction mechanism between two fingers which are applied at one side and the other of the base and which press on the finger supports 64 whilst, using another finger, he depresses the pushing member. This then moves along the length of the needle.

More precisely, the open end of the pushing member is supported on the skin of the patient, whilst the base is caused to move upwards along the length of the pushing member. The needle is thus progressively lowered inside the pushing member until it is moved into the position illustrated in FIG. 7 in which the main portion 35 of the needle extends completely inside the pushing member and is protected, preventing any risk of an occurrence of accidental pricking.

It is envisaged that, with an injection device of this type, since the extraction mechanism is integrated permanently with the needle support and with the injection needle, any risk of loss is prevented. Furthermore, since the extraction mechanism can be folded down on the needle support, it does not impede the movements of the patient or the fixing of the injection device to the skin of the patient.

The invention claimed is:

1. An injection device comprising:
   a needle support;
   an injection needle joined to the needle support, the injection needle having a main portion with a free end, the free end being spaced from the needle support; and
   an extraction mechanism for extracting the injection needle, the extraction mechanism including:
      a base permanently articulated with the needle support, the base being movable between an inactive position of the extraction mechanism and an active position of the extraction mechanism;
      a pushing member movable relative to the base between a first position in which the needle is extended and a second position in which the needle is retracted with the free end received in the pushing member; and
      an engagement member configured to releasably hold the extraction mechanism in the active position,
   wherein the pushing member lies along an axis of the main portion of the injection needle when the extraction mechanism is in the active position,
   wherein a hollow portion is defined in the base, the hollow portion constituting a passage for allowing movement of the pushing member,
   wherein the pushing member is disposed in the passage such that the pushing member is slidably movable between the first position and the second position, and
   wherein the base is connected to the needle support by a joint such that the base is rotatable relative to the needle support about an articulation axis, the articulation axis being perpendicular to the injection needle.

2. The injection device according to claim 1, wherein the injection needle is mounted on a head at the end of the needle support, the head being visible in the inactive position of the extraction mechanism.

3. The injection device according to claim 2,
   wherein the head projects longitudinally out of the extraction mechanism and perpendicularly to the main portion of the injection needle in the inactive position of the extraction mechanism, and
   wherein the head is received in the pushing member in the active position of the extraction mechanism.

4. The injection device according to claim 1,
   wherein the pushing member is generally elongate, and
   wherein the pushing member extends in a plane which is generally perpendicular relative to the main portion of the needle when the base is in the inactive position of the mechanism.

5. The injection device according to claim 1,
   wherein the pushing member is generally hollow, and
   wherein the needle support comprises a core which is at least partially received in the pushing member when the base is in the inactive position of the mechanism.

6. The injection device according to claim 1, wherein the needle support and the base comprise complementary resilient engagement members configured to temporarily retain the base relative to the needle support in the inactive position of the extraction mechanism.

7. The injection device according to claim 1, wherein the base comprises radial extensions which form finger supports.

8. The injection device according to claim 1, wherein the pushing member can be moved in a sliding manner relative to the base.

9. The injection device according to claim 1, wherein the base and the pushing member comprise complementary resilient engagement members configured to retain the pushing member relative to the base in the position thereof in which the needle is refracted and/or in the position thereof in which the needle is extended.

10. The injection device according to claim 1,
    wherein the needle support comprises a central core, and
    wherein the pushing member has an aperture opening into a cavity which extends along the length of the pushing member, the cavity receiving the central core in the inactive position of the extraction mechanism, and the cavity being configured to receive the main portion of the needle in the active position of the extraction mechanism.

11. The injection device according to claim 1,
    wherein the injection needle is fixedly joined to an end of the needle support beyond the articulation axis and along an axis of the support.

12. The injection device according to claim 1, wherein the base delimits the passage for movement of the pushing member.

13. The injection device according to claim 1,
    wherein the injection needle is fixedly joined to an end of the needle support which extends away from the articulation axis, and
    wherein a portion of the injection needle extends inside the needle support along a longitudinal axis of the support.

14. The injection device according to claim 1, wherein the pushing member is disposed within the base, and
    wherein the pushing member is slidable through the base between the first position and the second position.

15. An injection device comprising:
    a needle support;
    an injection needle joined to the needle support, the injection needle having a main portion with a free end, the free end being spaced from the needle support; and
    an extraction mechanism for extracting the injection needle, the extraction mechanism including:
       a base connected to the needle support, the base being movable relative to the needle support between an inactive position of the extraction mechanism and an active position of the extraction mechanism;
       a pushing member movable relative to the base between a first position in which the needle is extended and a second position in which the needle is retracted with the free end received in the pushing member; and
    wherein a longitudinal axis of the pushing member is parallel to a longitudinal axis of the main portion of the injection needle when the extraction mechanism is in the active position,
    wherein a hollow portion is defined in the base, the hollow portion constituting a passage for allowing movement of the pushing member, wherein the pushing member is disposed in the passage such that the pushing member is slidably movable between the first position and the second position, and wherein the base is connected to the needle support by a joint such that the base is rotatable relative to the needle support about an articulation axis, the articulation axis being perpendicular to the injection needle.

16. The injection device according to claim 15, further comprising an engagement member configured to releasably hold the extraction mechanism in the active position.

17. The injection device according to claim 15, wherein the base and the pushing member comprise complementary resilient engagement members configured to retain the pushing member relative to the base in the position thereof in which the needle is refracted and/or in the position thereof in which the needle is extended.

18. The injection device according to claim 15,
wherein the injection needle is fixedly joined to an end of the needle support which extends away from the articulation axis, and
wherein a portion of the injection needle extends inside the needle support along a longitudinal axis of the support.

19. The injection device according to claim 15, wherein the pushing member is disposed within the base, and
wherein the pushing member is slidable through the base between the first position and the second position.

* * * * *